United States Patent [19]

Burkard et al.

[11] 4,226,865
[45] Oct. 7, 1980

[54] METHOD OF TREATING DEPRESSION

[75] Inventors: Willy Burkard, Reinach; Pierre-Charles Wyss, Muttenz, both of Switzerland

[73] Assignee: Hoffmann-La Roche Inc., Nutley, N.J.

[21] Appl. No.: 907,366

[22] Filed: May 19, 1978

Related U.S. Application Data

[62] Division of Ser. No. 771,222, Feb. 23, 1977, abandoned.

[30] Foreign Application Priority Data

Mar. 8, 1976 [AT] Austria ................................. 1674/76

[51] Int. Cl.³ .......................................... A61K 31/535
[52] U.S. Cl. ................................... 424/248.5; 544/160
[58] Field of Search ....................... 424/248.5; 544/160

[56] References Cited

U.S. PATENT DOCUMENTS 3,502,652  3/1970  Jucker et al. ......................... 544/169
3,787,419  1/1974  Bruce .............................. 424/248.54

FOREIGN PATENT DOCUMENTS 1501846 10/1967 France ...................................... 544/160

OTHER PUBLICATIONS

Reynaud et al., "Chem. Abstracts", vol. 75, (1971), No. 5429e, Abstract of Chim. Ther., (1971), vol. 6, pp. 25–41; p. 4248 of Chem. Abstracts Subject Index, (A–D), vol. 75, (1971).

Primary Examiner—Henry R. Jiles
Assistant Examiner—R. W. Ramsuer
Attorney, Agent, or Firm—Samuel L. Welt; George M. Gould; Peter R. Shearer

[57] ABSTRACT

Thiobenzamides of the formula

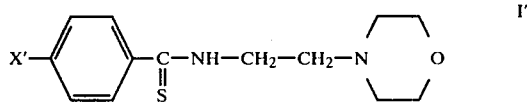

wherein X' is bromine, fluorine, iodine, trifluoromethyl or $C_{3-4}$ alkyl prepared from N-(2-aminoethyl)-morpholine and a compound of the formula

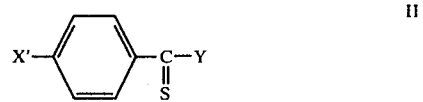

wherein
X' is as hereinbefore set forth and;
Y is methoxy or ethoxy are described. The end products, including p-chloro-N-(2-morpholinoethyl)-thiobenzamide, are useful in the treatment of depressive conditions, that is, are useful as antidepressants.

3 Claims, No Drawings

METHOD OF TREATING DEPRESSION

This is a division of application Ser. No. 771,222 filed Feb. 23, 1977, now abandoned.

BRIEF SUMMARY OF THE INVENTION

The invention relates to thiobenzamides characterized by the formula

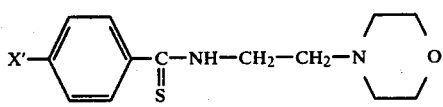

wherein X' is bromine, fluorine, iodine, trifluoromethyl or $C_{3-4}$ alkyl or pharmaceutically acceptable acid addition salts thereof.

In another aspect, the invention relates to pharmaceutical preparations having mono-amine oxidase inhibiting activity comprising a compound of the formula

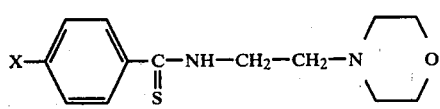

wherein X is halogen, trifluoromethyl or $C_{3-4}$ alkyl or a pharmaceutically acceptable acid addition salt thereof.

In still another aspect, the invention relates to the use of the compounds of formula I as agents in the treatment of depression, i.e., as antidepressants.

DETAILED DESCRIPTION OF THE INVENTION

In accordance with the invention, thiobenzamides of the formula

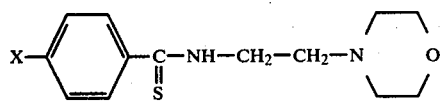

wherein X is halogen, trifluoromethyl or $C_{3-4}$ alkyl and pharmaceutically acceptable acid addition salts thereof have been found to possess monoamine oxidase (MAO) inhibiting activity.

More specifically, in one aspect the invention relates to pharmaceutical preparations having MAO inhibiting activity, said preparations containing as an essential active ingredient a compound of formula I hereinbefore or a pharmaceutically acceptable acid addition salt thereof.

In another aspect, the invention relates to a method of treating depressive conditions with a compound of the formula

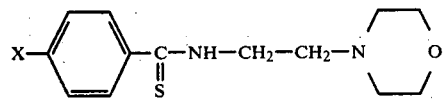

wherein X is halogen, trifluoromethyl or $C_{3-4}$ alkyl or a pharmaceutically acceptable acid addition salt thereof.

The invention also relates to compounds characterized by the formula

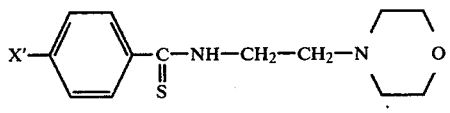

wherein X' is bromine, fluorine, iodine, trifluoromethyl or $C_{3-4}$ alkyl or pharmaceutically acceptable acid addition salts thereof.

The term "halogen" denoted by X is chlorine, fluorine, bromine or iodine with chlorine being preferred. $C_{3-4}$ alkyl is a straight-chain or branched-chain alkyl group containing 3 or 4 carbon atoms, namely, n-propyl, isopropyl, n-butyl, isobutyl, 1-methylpropyl or t-butyl.

The thiobenzamide of formula I wherein X is chlorine, namely, p-chloro-N-(2-morpholinoethyl)thiobenzamide, is a known compound which is described in French Pat. No. 1,501,846.

The thiobenzamides of formula I form addition salts at the nitrogen atom of the morpholino residue with organic or inorganic acids. Exemplary of such salts are hydrohalides, for example, hydrochlorides; phosphates; alkylsulfonates, for example, ethanesulfonates; monoarylsulfonates, for example, toluenesulfonates; acetates; citrates; benzoates and the like.

Preferred thiobenzamides of formula I are those in which X is halogen.

An especially preferred thiobenzamide of formula I is p-chloro-N-(2-morpholinoethyl)-thiobenzamide.

Other preferred thiobenzamides of formula I are p-bromo-N-(2-morpholinoethyl)thiobenzamide and p-t-butyl-N-(2-morpholinoethyl)-thiobenzamide.

The thiobenzamides of formula I' hereinbefore and their acid addition salts can be prepared by reacting N-(2-aminoethyl)-morpholine with a compound of the formula

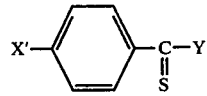

wherein X' is as previously described and Y is methoxy or ethoxy and, if desired, converting a thiobenzamide of formula I' obtained into a pharmaceutically acceptable acid addition salt thereof.

The reaction of N-(2-aminoethyl)-morpholine with a compound of formula II is conveniently carried out in the absence of solvent at a temperature in the range of from about room temperature to about 140° C., preferably at about 90° C.

The compounds of formula II are known compounds or are analogs of known compounds and can be prepared by known procedures. Thus, for example, a benzonitrile of the formula

wherein X' is as previously described can be reacted in the presence of hydrogen chloride gas with methanol or ethanol to give the hydrochloride of the corresponding benzimidate of the formula

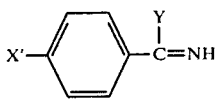

wherein X' and Y are as previously described. Then, the resulting hydrochloride can be converted into the desired compound of formula II with hydrogen sulfide in the presence of pyridine.

As mentioned earlier, the thiobenzamides of formula I and their pharmaceutically acceptable acid addition salts possess monoamine oxidase (MAO) inhibiting activity. Due to this activity, the thiobenzamides of formula I and their pharmaceutically acceptable acid addition salts are useful in the treatment of depressive conditions. Stated another way, the compounds of formula I are useful as antidepressants.

The MAO inhibiting activity of the thiobenzamides of formula I can be demonstrated using standard methods. Thus, the thiobenzamides of formula I to be tested were administered p.o. to rats. One hour after the administration, the rats were killed and the MAO inhibiting activity in the liver homogenates was measured according to the method in Biochem. Pharmacol. 12, pp. 1439–1441 (1963). The thus determined activity of representative thiobenzamides of formula I as well as their toxicity is evident from the $ED_{50}$ values ($\mu$mol/kg, p.o. in the rat) or $LD_{50}$ values (mg/kg, p.o. in the mouse) listed in the Table which follows:

TABLE

| Thiobenzamide | $ED_{50}$ | $LD_{50}$ |
| --- | --- | --- |
| p-Chloro-N-(2-morpholinoethyl)-thiobenzamide | 2 | 1250–2500 |
| p-Bromo-N-(2-morpholinoethyl)-thiobenzamide | 2 | 1250–2500 |
| p-t-Butyl-N-(2-morpholinoethyl)-thiobenzamide | 10 | >5000 |

The thiobenzamides of formula I and their pharmaceutically acceptable acid addition salts can be used as medicaments, for instance, in the form of pharmaceutical preparations which contain them in association with a pharmaceuticaly acceptable carrier material. Such carrier material can be an organic or an inorganic inert carrier material which is suitable for enteral, for example, oral, or parenteral administration, such as water, gelatin, gum arabic, lactose, starch, magnesium stearate, talc, vegetable oils, polyalkyleneglycols or the like. The pharmaceutical preparations can be made up in solid form, for example, as tablets, dragees, suppositories or in liquid form, for example, as solutions, suspensions or emulsions. The pharmaceutical preparations may be sterilized and/or may contain compatible adjuvants such as preservatives, stabilizing agents, wetting or emulsifying agents, salts for modifying the osmotic pressure or buffering agents. The pharmaceutical preparations may also contain other therapeutically valuable materials.

Appropriate pharmaceutical dosage forms contain from about 1 mg. to 100 mg. of a thiobenzamide of formula I or of a pharmaceutically acceptable acid addition salt thereof. Appropriate oral dosage ranges are from about 0.1 mg/kg per day to about 5 mg/kg per day. Appropriate parenteral dosage ranges are from about 0.01 mg/kg per day to about 0.5 mg/kg per day. These ranges can be increased or decreased according to individual requirements and the directions of the attending physician. Oral administration is preferred.

The examples which follow further illustrate the present invention. All temperatures are in degrees Centigrade, unless otherwise stated.

EXAMPLE 1

Preparation of p-t-butyl-N-(2-morpholinoethyl)-thiobenzamide 10.6 g. of O-ethyl-p-t-butyl-thiobenzoate and 6.2 g. of N-(2-aminoethyl)-morpholine are heated at 90° C. for 2 hours. Then, the mixture is cooled to room temperature, treated with 50 ml. of ice-water and, while cooling with ice-water and stirring, is acidified with 3-N hydrochloric acid. Thereafter, the solution is extracted with two 100 ml. portions of diethyl ether and the aqueous phase is made basic with ammonia while cooling with ice-water and stirring. The crystalline product is removed by filtration and washed with cold water and diethyl ether. After recrystallization from ethyl acetate/hexane, there is obtained 6.7 g. of p-t-butyl-N-(2-morpholinoethyl)-thiobenzamide having a melting point of 129° C.

The O-ethyl-p-t-butyl-thiobenzoate used as the starting material can be prepared as follows:

A solution of 41.2 g. of p-t-butylbenzonitrile in 450 ml. of absolute ethanol is saturated with hydrogen chloride gas while cooling with ice-water and then is left to stand overnight at 4° C. Thereafter, the mixture is evaporated to dryness and the residue further evaporated with three 300 ml. portions of ethanol. The solid residue is triturated with 500 ml. of diethyl ether and filtered. After recrystallization from ethanol/diethyl ether, there are obtained 56.1 g. of ethyl p-t-butylbenzimidate hydrochloride having a melting point of 116° C.

25 g. of ethyl p-t-butylbenzimidate hydrochloride are dissolved in 65 ml. of pyridine saturated with hydrogen sulfide. Hydrogen sulfide is subsequently conducted through the solution for 6 hours while cooling with ice-water. The mixture is allowed to stand overnight at 4° C. While cooling with ice-water and stirring, the mixture is subsequently treated successively with 50 ml. of ice-water, 90 ml. of concentrated hydrochloric acid and 90 g. of ice and then extracted with three 200 ml. portions of diethyl ether. The ether solution is washed with hydrochloric acid, dried over potassium carbonate, evaporated and distilled (100° C., 0.04 Torr), and there are obtained 21 g. of O-ethyl-p-t-butyl-thiobenzoate.

EXAMPLE 2

Preparation of p-bromo-N-(2-morpholinoethyl)-thiobenzamide hydrochloride 6.1 g. of O-ethyl-p-bromo-thiobenzoate and 3.25 g. of N-(2-aminoethyl)-morpholine are heated at 90° C. for 2 hours. Then, the mixture is cooled to room temperature, treated with 25 ml. of ice-water and, while cooling with ice-water and stirring, acidified with 3-N hydrochloric acid. The precipitated product is then removed by filtration and washed with water and diethyl ether. After recrystallization from methanol, there are obtained 3.7 g. of p-bromo-N-(2-morpholinoethyl)-thiobenzamide hydrochloride having a melting point of 231° C.

EXAMPLE 3

Tablets of the following composition are prepared in a manner known per se:

| | |
|---|---|
| p-chloro-N-(2-morpholinoethyl)-thiobenzamide | 50.0 mg. |
| Lactose | 95.0 mg. |
| Maize starch | 100.0 mg. |
| Talc | 4.5 mg. |
| Magnesium stearate | 0.5 mg. |
| Weight of one tablet | 250.0 mg. |

In place of p-chloro-N-(2-morpholinoethyl)-thiobenzamide, there can also be used, for example, as the active ingredient, p-bromo-N-(2-morpholinoethyl)-thiobenzamide or p-t-butyl-N-(2-morpholinoethyl)-thiobenzamide.

We claim:

1. A method of treating a depressive condition which comprises administering to a host requiring such treatment an antidepressive amount of a compound of the formula

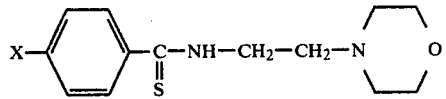

wherein X is halogen, trifluoromethyl or $C_{3-4}$ alkyl or a pharmaceutically acceptable acid addition salt thereof.

2. A method in accordance with claim 1 wherein there is administered a compound of the formula

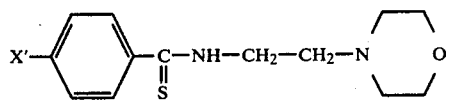

wherein X' is bromine, fluorine, iodine, trifluoromethyl or $C_{3-4}$ alkyl or a pharmaceutically acceptable acid addition salt thereof.

3. A method in accordance with claim 1 wherein the compound is p-chloro-N-(2-morpholinoethyl)-thiobenzamide or a pharmaceutically acceptable acid addition salt thereof.

* * * * *